(12) United States Patent
Nair et al.

(10) Patent No.: US 7,658,937 B2
(45) Date of Patent: Feb. 9, 2010

(54) ANTHRAQUINONES AND PROCESS FOR THE PREPARATION AND METHOD OF USE THEREOF

(75) Inventors: Muraleedharan G. Nair, Okemos, MI (US); Mugunthu R. Dhananjeyan, Toledo, OH (US); Michael A. Kron, Okemos, MI (US); Youli P. Milev, DeWitt, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 468 days.

(21) Appl. No.: 11/074,227

(22) Filed: Mar. 7, 2005

(65) Prior Publication Data

US 2005/0267307 A1 Dec. 1, 2005

Related U.S. Application Data

(60) Provisional application No. 60/570,109, filed on May 11, 2004, provisional application No. 60/650,552, filed on Feb. 7, 2005.

(51) Int. Cl.
| | |
|---|---|
| *A01N 25/00* | (2006.01) |
| *A01N 37/02* | (2006.01) |
| *A01N 37/06* | (2006.01) |
| *A61K 31/22* | (2006.01) |
| *A61K 31/225* | (2006.01) |

(52) U.S. Cl. .................. 424/405; 514/546; 514/547; 514/548

(58) Field of Classification Search ............... 424/405; 514/516, 548; 552/208, 261, 262, 267
See application file for complete search history.

(56) References Cited

U.S. PATENT DOCUMENTS

| | | | |
|---|---|---|---|
| 3,870,655 A | 3/1975 | Nanba | |
| 4,379,092 A | 4/1983 | Devic | |
| 6,800,615 B2 | 10/2004 | Cichewicz et al. | |
| 6,835,443 B2 | 12/2004 | Teshima et al. | |
| 2004/0106686 A1 | 6/2004 | Cichewicz et al. | |
| 2004/0152645 A1 | 8/2004 | Cichewicz et al. | |

FOREIGN PATENT DOCUMENTS

JP 61100543 5/1986

OTHER PUBLICATIONS

Dhananjeyan et al., "Synthesis and Activity of Substituted Anthraquinones against HUman Filarial Parasite, *Brugia malayi*", Journal of Medicincal Chemistry, Apr. 21, 2005, 48(8), pp. 2822-2830.*
Ottesen, E.A., Trop. Med. Int. Hlth. 5, 591-594 (2000).
Cichewicz,R.H., et al., Tetrahedron 58, 8597-8606(2002).
Nasman,J-H. N., synthesis 788-789(1985).
Rodriguez, F., et al., Separation Science and Technology 24 275-289 1989.
Boisvert, L., J. Org. Chem. 53 4052-4059 (1988).
Bensari, A., et al., Synthesis 267-271 (2003).
Kotsuki, H., et al., Synthesis 603-606(1999).
Kobayashi, S., Eur. J. Org: Chem. 15-27(1999).
Yang, P., et al., Huaxue Shijie 34 258-260 (1993).
Huffman, J. W., et al., J. Org. Chem.,37 487-490 (1972).
Asaoka, M., et al., Chem. Lett. 167-170(1977).
Eliel, E. L., et al., J. Am. Chem. Soc., 77 5092-5095(1955).
Pratt, D.S., et at., J. Am. Chem Soc. 40 219-214(1918).

* cited by examiner

*Primary Examiner*—Traviss C McIntosh, III
(74) *Attorney, Agent, or Firm*—Ian C. McLeod (57) ABSTRACT

A process for the preparation of hydroxyl substituted anthraquinones is described. The process couples a phthalic anhydride (substituted or unsubstituted) to benzene ring moiety substituted with at least two hydroxyl groups. Remaining hydroxy groups were converted to methoxy groups in some anthraquinones. The compounds are particularly useful for the treatment of parasitic diseases. Also, a method of treating or preventing malaria, filariasis schistosomiasis and other parasitic diseases using anthraquinones.

5 Claims, 9 Drawing Sheets

| | Phenol 2 | Anthraquinones |
|---|---|---|
|  1a |  |  A |
| |  |  D |
| |  |  E |
|  1 |  |  A |
| |  |  F |

Figure 3

(i) Ac$_2$O/H$_2$SO$_4$; (ii) C(CH$_3$)COCl/Et$_3$N;

(iii) Maleic anhydride/Ether; (iv) H$_2$SO$_4$ at −10 °C

Figure 4

| Anthraquinone | Methylating Agent | Product |
|---|---|---|
|  | CH$_2$N$_2$ |  |
| | (CH$_3$)$_2$SO$_4$ | <br>P |
|  | CH$_2$N$_2$ | <br>Q |
| | (CH$_3$)$_2$SO$_4$ | <br>R |
|  | CH$_2$N$_2$ | <br>S |
| | (CH$_3$)$_2$SO$_4$ | <br>S |

ANTHRAQUINONES AND PROCESS FOR THE PREPARATION AND METHOD OF USE THEREOF

CROSS-REFERENCE TO RELATED APPLICATIONS

This application claims priority to U.S. Provisional Application Ser. No. 60/570,109, filed May 11, 2004 and Provisional Application Ser. No. 60/650,552, filed Feb. 7, 2005.

STATEMENT REGARDING FEDERALLY SPONSORED RESEARCH OR DEVELOPMENT

This invention was funded under National Institutes of Health Cooperative Agreement U01-A1153877-02(MK) NIHR21TW0662501. The U.S. Government has certain rights to this invention.

STATEMENT REGARDING GOVERNMENT RIGHTS

Not Application

BACKGROUND OF THE INVENTION (1) Field of the Invention

The present invention relates to novel hydroxy substituted anthraquinones and to processes for preparing these compounds. The anthraquinones can also be methoxy substituted in place of hydroxyl groups. These compounds are particularly useful in treatments for malaria, schistosomiasis and elephantiasis (filariasis) helminthic and other parasitic diseases. Certain novel anthraquinones are described.

(2) Description of Related Art

There are many parasitic diseases. Lymphatic filariasis (elephantiasis) in particular is a devastating disease caused by *Wuchereria bancrofti* and *Brugia malayi* spp. The World Health Organization estimates that 120 million people globally are affected and at least 40 million are disabled both physically and psychosocially. This is one of the major public health problems with socioeconomic impacts in Africa, Asia, the Western Pacific and the Americas (Ottesen, E. A., *Trop. Med. Int. Hlth.* 5, 591-594 (2000)). About 90% of these infections are caused by *Wuchereria bancrofti*, and the remainder by *Brugia* spp. Humans are the only host for *W. bancrofti* (Anonymous, The Global Alliance for the Elimination of lymphatic Filariasis—epidemiology. Http://www.filariasis.org /2002)).

Numerous quinones including dihydroxy- and trihydroxy-anthraquinones are widely distributed in plant kingdom and contribute to pigmentation in plants (Thomson, R. H., *Naturally Occurring Quinonones*, Academic press, pp 367-535, London (1971)). *Hemerocallis fulva* kwanza kaempfer (daylily) roots was reported to contain several anthraquinone derivatives, naphthaline glycosides and flavones (Cichewicz, R. H., et al., Tetrahedron 58, 8597-8606 (2002)). In our earlier studies, some of the anthraquinones isolated from daylily roots were found to be active against *Schistosoma mansoni*, one of the *Schistosoma* spp. parasites responsible for schistosomiasis (Cichewicz, R. H., et al., Tetrahedron 58 8597-8606 (2002)). Schistosomiasis is also a debilitating disease caused by parasitic trematodes of the genus *Schistosoma* that afflicts 200 million people worldwide. These active anthraquinones from daylily roots were assayed against filarial parasite (*Brugia malayi*) and were found to, be active. The presence of these active anthraquinones in daylily roots is very small.

It is also essential to explore the possible utility of these active and anthraquinone analogues as prophylactic and/or therapeutic agent for parasitic diseases. Therefore, it is a necessity to synthesize these anthraquinones to further evaluate their efficacy in vivo and determine the toxicity in order to determine their potential as therapeutic drugs for filariasis and schistosomiasis.

The production of anthraquinones was reported by the catalytic oxidation of anthracene obtained from coal tar (Nanba, Y., et al., U.S. Pat. No. 3,870,655; 1975; and Rodriguez, F., et al., Separation Science and Technology 24 275-289 1989). It has also been prepared by Diels-Alder cycloaddition and Friedel-Crafts acylation reactions using suitable reagents. The Diels-Alder reaction between 1,4-napthaquinone and 1,3-diene followed by dehydrogenation of the resulting tricyclic adduct yielded anthraquinones (Boisvert, L., J. Org. Chem. 53 4052-4059 (1988)). However, production of 1,4-naphthaquinone and 1,3-dienes are complex and costly.

The Friedel-Crafts acylation reaction is one of the most commonly used reactions in synthetic organic chemistry, which is catalyzed by Lewis acids such as $AlCl_3$, $BF_3$, $FeCl_3$, $TiCl_4$ and $Sc(OTf)_3$ (Olah, G. A., *Friedel-Crafts and related reactions*, Wiley Interscience, NY, Vol II, part I (1964); Bensari, A., et al., Synthesis 267-271 (2003); Kotsuki, H., et al., Synthesis 603-606 (1999); and Kobayashi, S., Eur. J. Org. Chem. 15-27 (1999)). The mechanism involves the formation of an acylium ion intermediate that are generated by the reaction between carboxylic acid derivatives and the acid catalyst.

Another method for the preparation of anthraquinones was reported by the condensation of phthalic anhydride and benzene using an equimolecular amount of HF and $BF_3$ as catalysts. The resulting o-benzoylbenzoic acid was then converted to corresponding anthraquinone by heating it with concentrated sulfuric acid or other means of cyclisation. The drawbacks of this method included were the purification of o-benzoylbenzoic acid from crude reaction mixture, poor yield and the formation of sulfonated products (Devic, M., U.S. Pat. No. 4,379,092 (1983)). In order to avoid these disadvantages, the reaction was attempted under gaseous phase over a solid catalyst such as silico-aluminate (Yang, P., et al., Huaxue Shijie 34 258-260 (1993)) or titanium oxide Akazawa, Y., JP 61100543 (1986)). However, these processes required high temperature and expensive installations.

OBJECTS

It is therefore an object of the present invention to provide novel hydroxy substituted anthraquinones or methoxy derivatives thereof. Further, it is an object of the present invention to provide novel treatment of various diseases using hydroxy substituted anthraquinones or derivatives. Further still, it is an object of the present invention to provide a process for the preparation of such compounds. These and other objects will become increasingly apparent by reference to the following description.

SUMMARY OF THE INVENTION

The present invention relates to a process for the preparation of an anthraquinone which comprises:

(a) reacting with heating in a reaction mixture a molar excess of a phthalic anhydride with a hydroxy substituted phenol in a molten anhydrous combination of a Lewis acid and an alkali metal halide salt;

(b) cooling the reaction mixture of step (a);

(c) adding an aqueous acid to the reaction mixture of step (b) to produce an acylated anthraquinone;

(d) refluxing the reaction mixture of step (c) to produce the anthraquinone; and (e) separating the anthraquinone from the reaction mixture.

Lewis acids are well known as discussed above. Preferred is anhydrous aluminum chloride. The preferred salt is sodium chloride; however, other halides (Br, I) can be used. The reaction is conducted anhydrously with essentially anhydrous reagents.

The reaction mixture is preferably heated at about 165° to 185° C. for between about 4 to 5 hours. The aqueous acid is preferably aqueous hydrochloric acid. The anthraquinone is preferably separated in step (e) by solvent extraction from the reaction mixture. The solvent is preferably ethyl acetate or diethyl ether. Preferably the separation of the anthraquinone is by chromatography.

The present invention also relates to a process for methylating a hydroxy substituted anthraquinone to produce a methoxy substituted anthraquinone which comprises:

(a) reacting in a reaction mixture the hydroxy substituted anthraquinone with N-nitroso-N-methylurea and potassium hydroxide in diethyl ether; and (b) separating the methoxy substituted anthraquinone from the reaction mixture. The methyl substituted anthraquinone is preferably a mono-methoxy substituted anthraquinone. The reaction mixture in step (a) is preferably cooled in an ice bath.

The diethyl ether is preferably evaporated from the reaction mixture, methoxy substituted anthraquinone is separated by extraction in a solvent and further separated by chromatography. The solvent is preferably selected from the group consisting of ethyl acetate and hexane.

Dimethyl sulfate in a dry solvent reacted with a dihydroxy anthraquinone can also be used to produce a dimethoxy anthraquinone. The solvent is then removed. The preferred solvent is acetone.

The present invention relates to an anthraquinone of the formula:

wherein $R_1$, $R_2$, $R_3$, $R_4$, $R_5$ and $R_6$ are selected from the group consisting of H, OH, $CH_3$ and $CH_3O$ and wherein at least one of $R_1$, $R_2$, $R_3$, $R_4$ and $R_5$ is $CH_3O$.

DESCRIPTION OF PREFERRED EMBODIMENTS

The compounds of the present invention are used in a method for inhibiting a parasite which comprises exposing the parasite to an inhibitory amount of a hydroxy substituted anthraquinone. U.S. Pat. Nos. 6,800,615 and 6,838,443, assigned to a common assignee, describes antihelminthic anthraquinones. U.S. patent application Ser. No. 10/723,671, now U.S Pat. No. 6,903,076, assigned to a common assignee, is a divisional application from U.S. Pat. No. 6,800,615, assigned to the common assignee. Ser. No. 10/761,071, filed Jan. 20, 2004, now U.S Pat. No. 7,132,403, is also a divisional application. Parasitic roundworms (nematodes), flatworms (cestodes) and flukes (trematodes) are responsible for billions of human, plant and animal infections throughout the world. Related parasites are causes of major economic loss as agricultural pests. Human parasitic nematodes include among other genera the filarial parasites (e.g. *Wuchereria bancrofti, Onchocerca volvulus, Brugia malayl, Brugia timori*, etc.) that cause hundreds of millions of cases of human disease such as river blindness and lymphatic filariasis. Attempts to prevent or cure animal disease caused by the filarial parasite *Dirofilaria immitis* (e.g. Dog heartworm) is a multimillion dollar industry in the U.S. alone. Dozens of other species of nematodes of human or veterinary importance include the hookworms, whipworms and Acarids that cause iron deficiency anemia, growth retardation, intestinal malabsorption and/or blockage. Human fluke infections include those caused by *Fasciola hepatica, Fasciola gigantica* and the agents of Schistosomiasis (*S. Japonicum, S. Mansoni, S. Haematobium* and *S. Mekongi*), and these flukes cause clinical disease ranging from hepatitis and abscess to bile duct obstruction, to granulomatous disease of the liver, kidneys, bladder and bowel. Human cestode infections include a wide variety of organisms that include *Echinococcus* species, *Taenia saginatia* and *T. Solium, Diphylobothrium latum*, and various other species of "tapeworms"Diseases caused by cestodes range from hydatid disease, to intestinal malabsorption and vitamin deficiency.

*Brugia malayi* spp., are the parasites which causes lymphatic filariasis or malaria. It has been found that they can be inhibited by the hydroxyl anthraquinones. The parasite can be inhibited in vitro. The parasite can be inhibited in vivo. The hydroxy substituted anthraquinone can also be methoxy substituted.

Anthraquinones have also been used to treat tumors. This is described in application Ser. No. 10/355,483, filed May 10, 2004, assigned to the common assignee.

Figure 1:
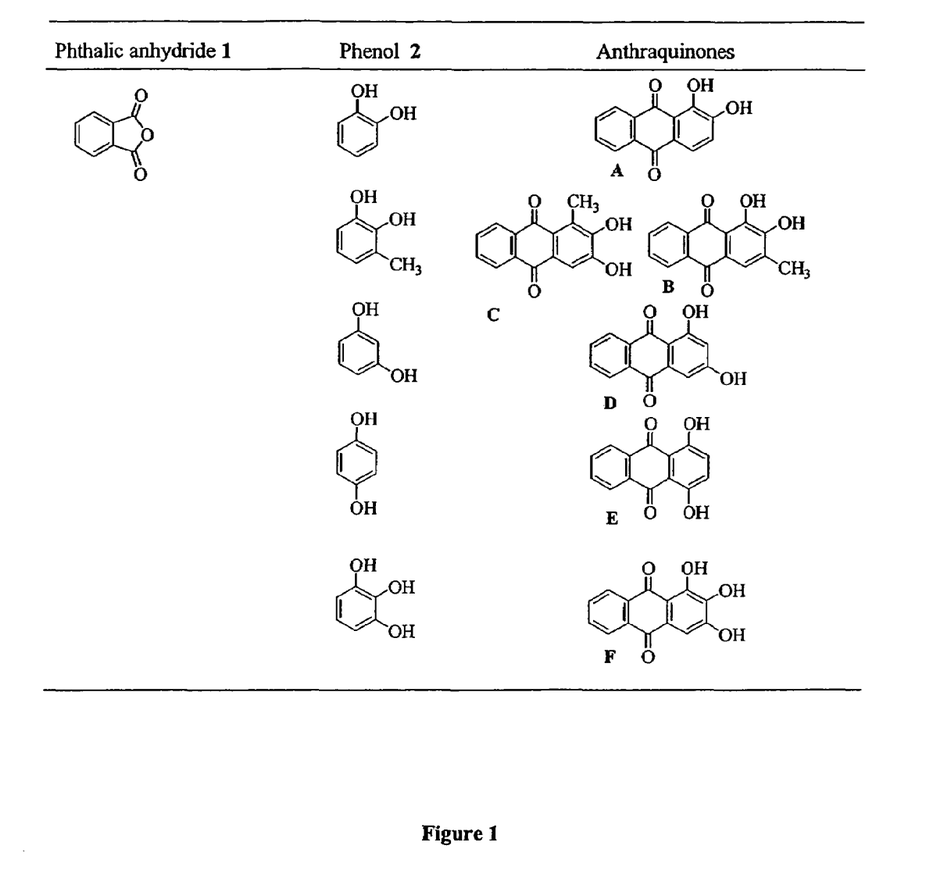
FIGS. 1, 2, 4 and 5 show anthraquinones produced by the process of the present invention and the intermediates used in the process.
Figure 2:
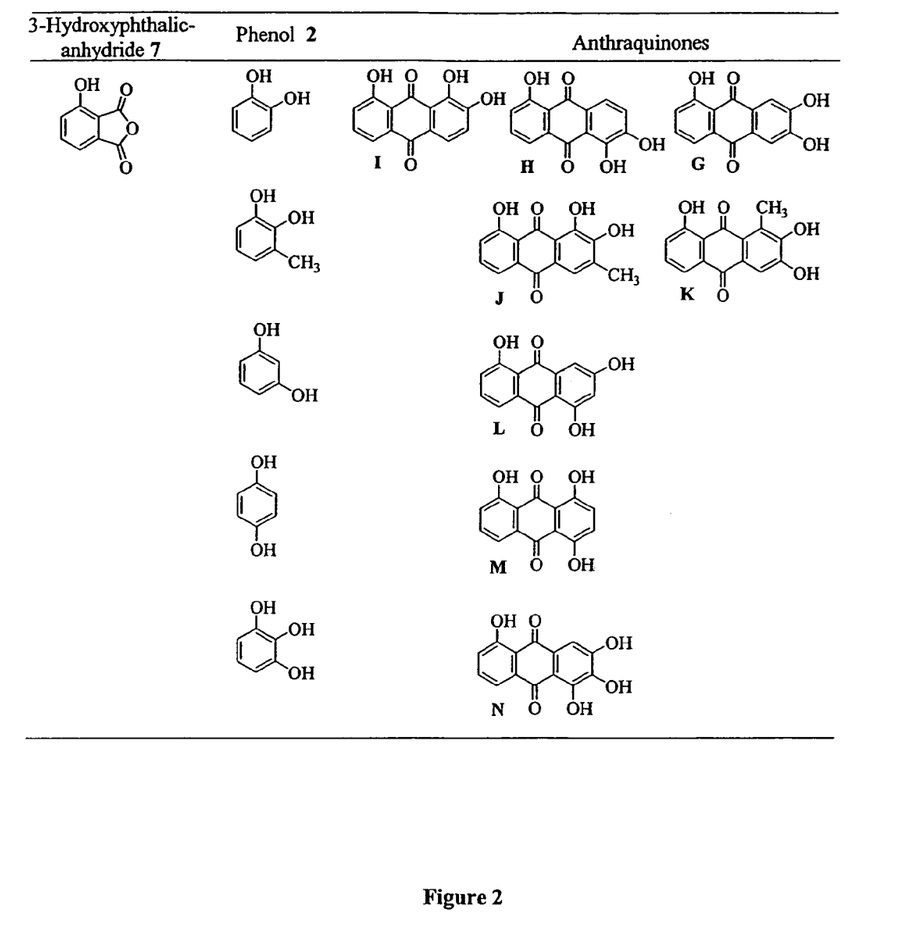
Figure 4:
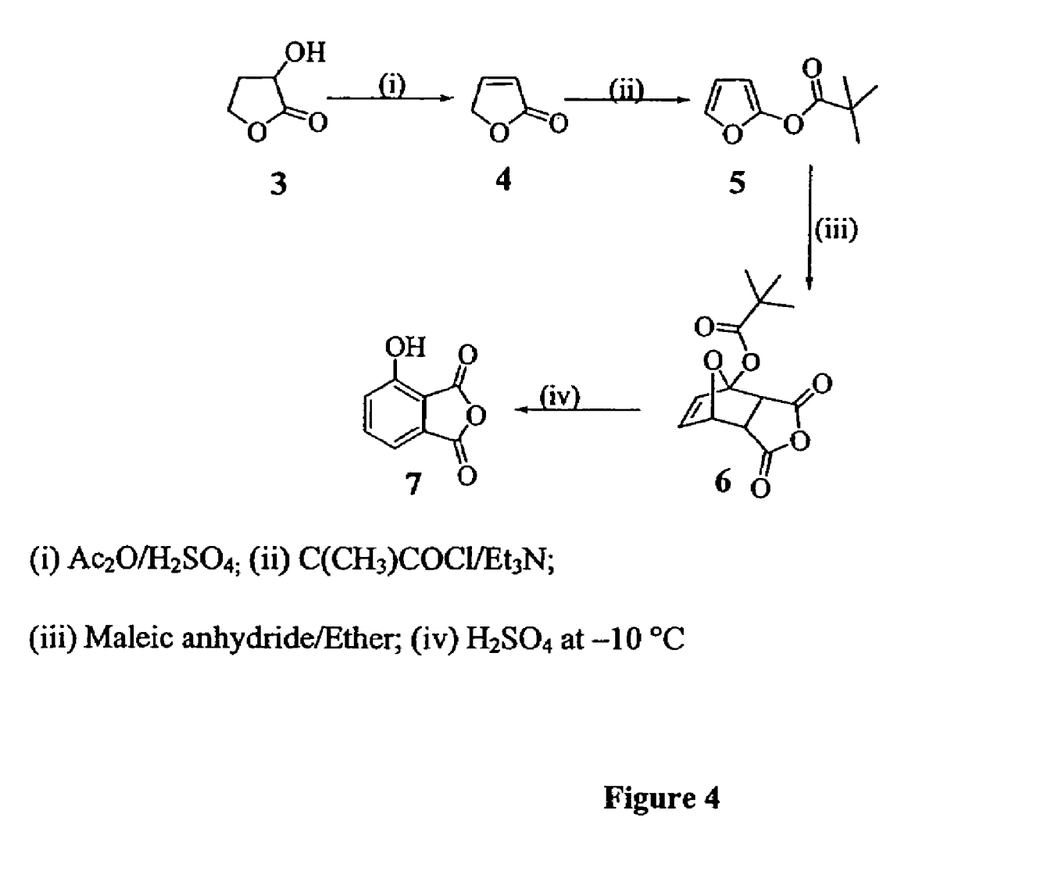
Figure 5:
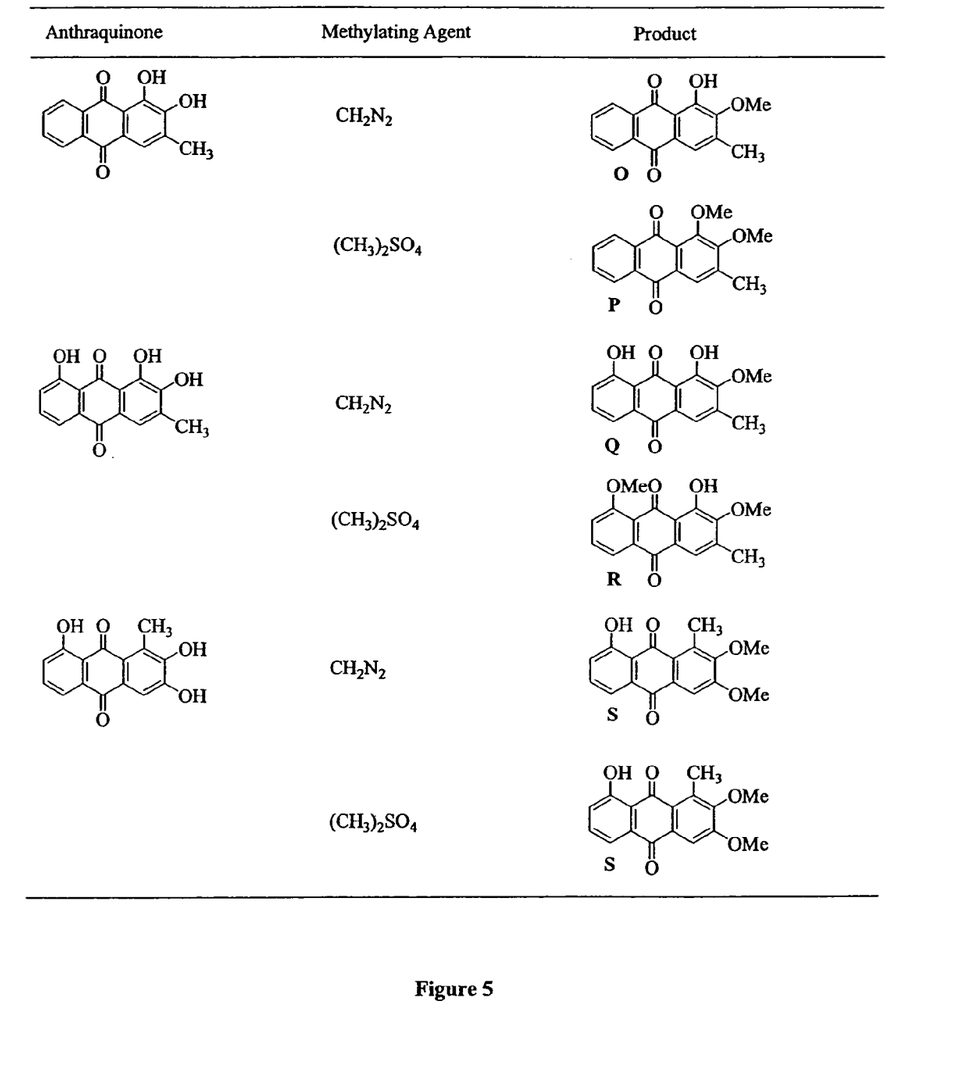
Figure 6:
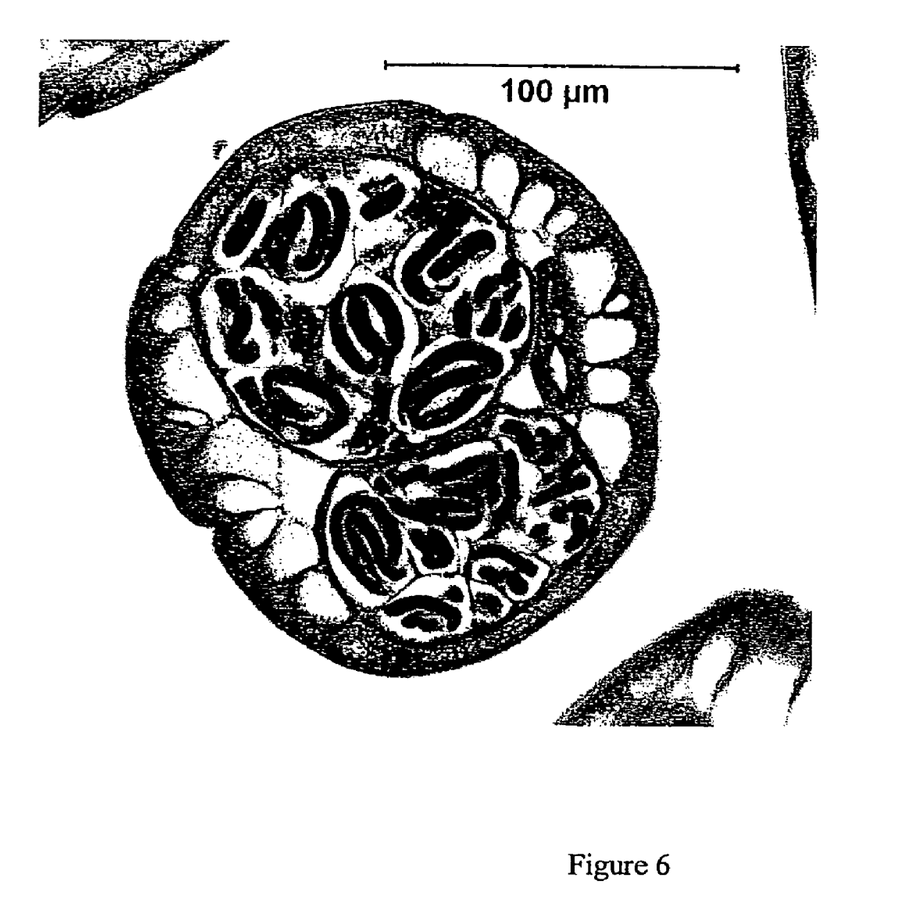
FIG. 6 is a cross-sectional view of H & E stained normal control adult female *Brugia malayi*. Normal duplicate intrauterine structures contains many well-formed microfilaria larvae that have not yet been released from the uterus. Magnification×400. Calibration mark indicates 100 microns in FIGS. 6-9).
Figure 7:
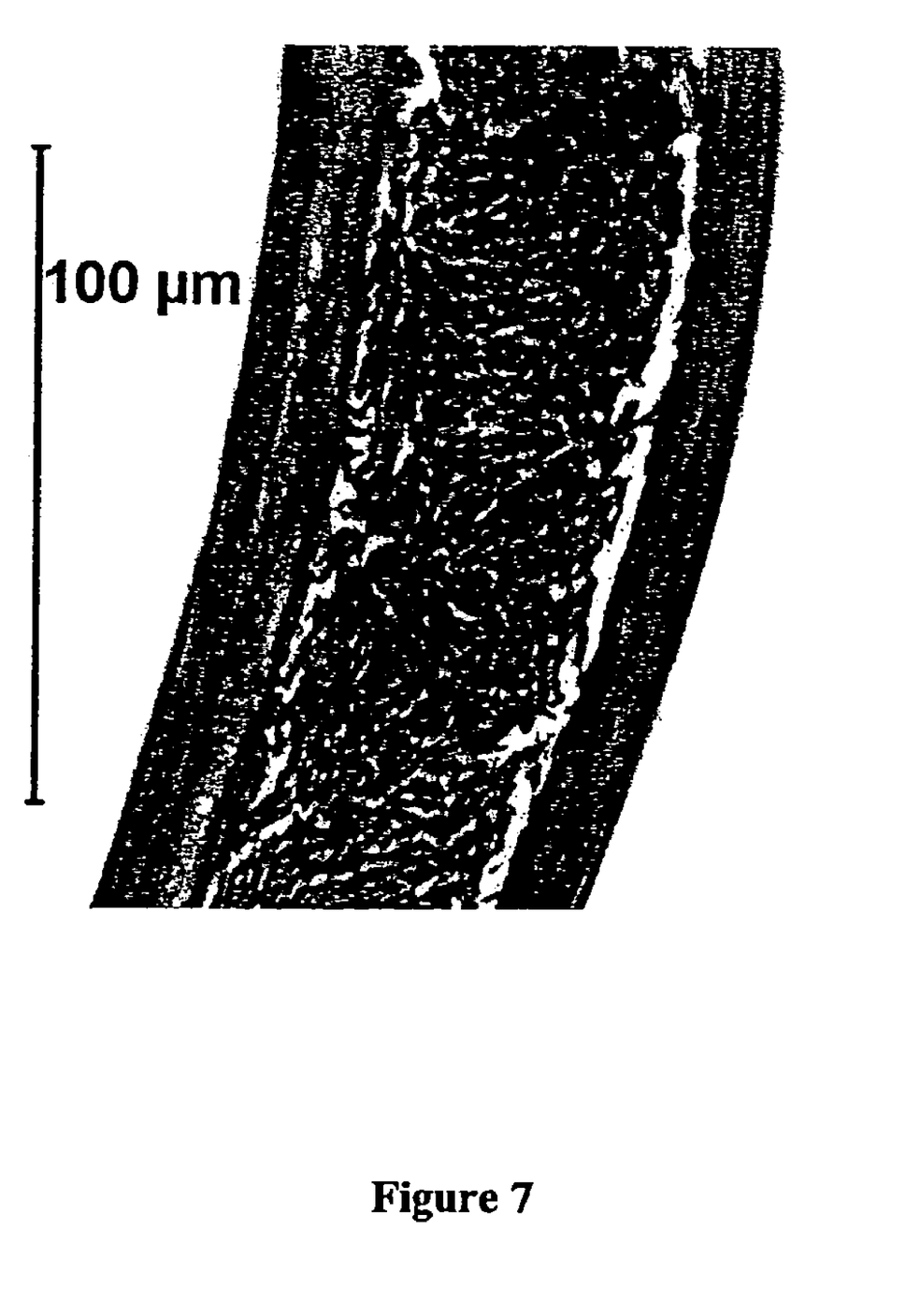
FIG. 7 is a longitudinal sectional view of normal adult male *B. malayi*. Section demonstrates well organized nuclei deep to the cuticle. Magnification×40.
Figure 8:
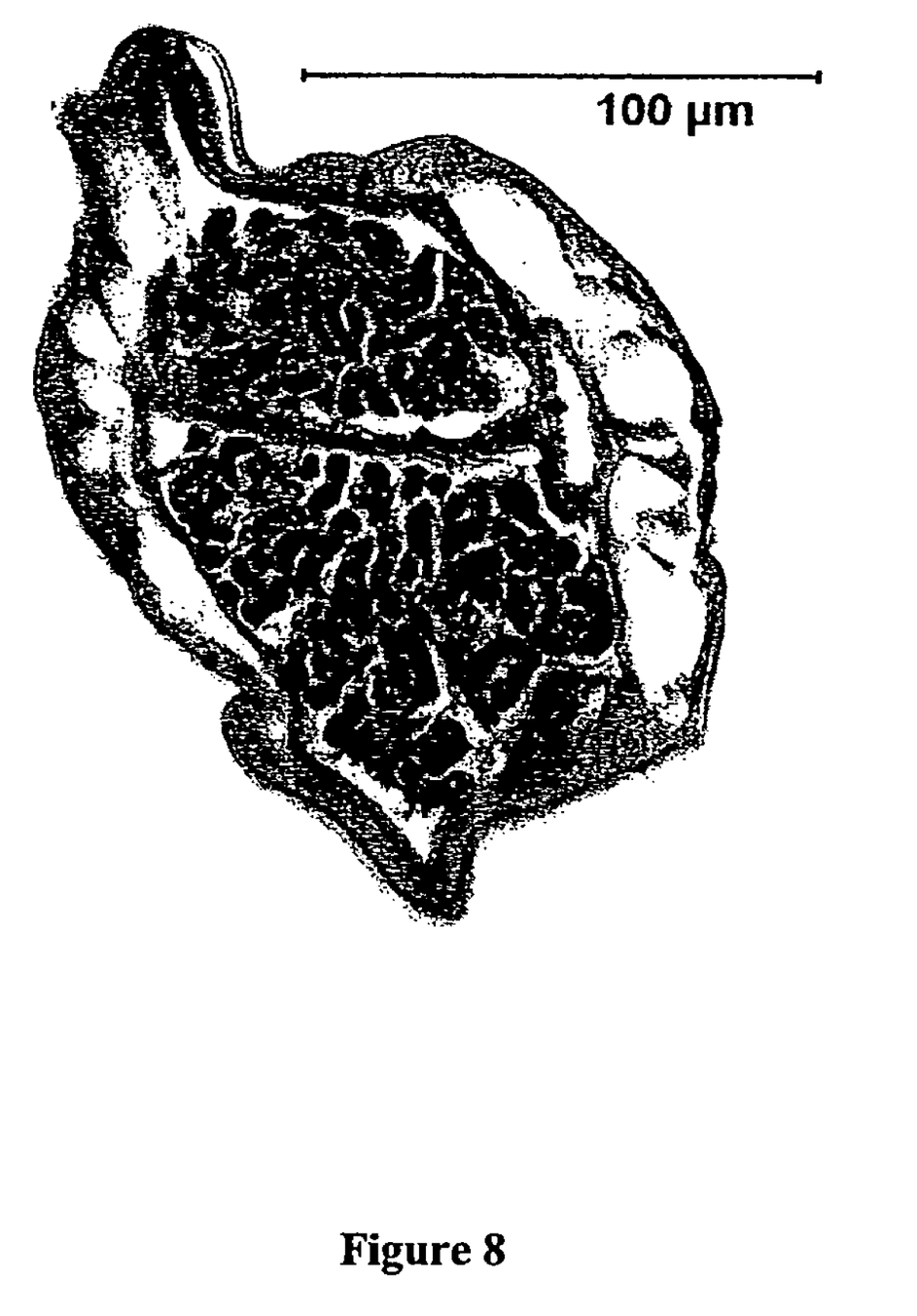
FIG. 8 is a cross-sectional view of the morphology of adult female *B. malayi* that has been killed by 5 ppm compound B. Note disruption of the stable cuticle and hypodermal regions, along with disorganization of the intrauterine microfilariae. Magnification×400.
Figure 9:
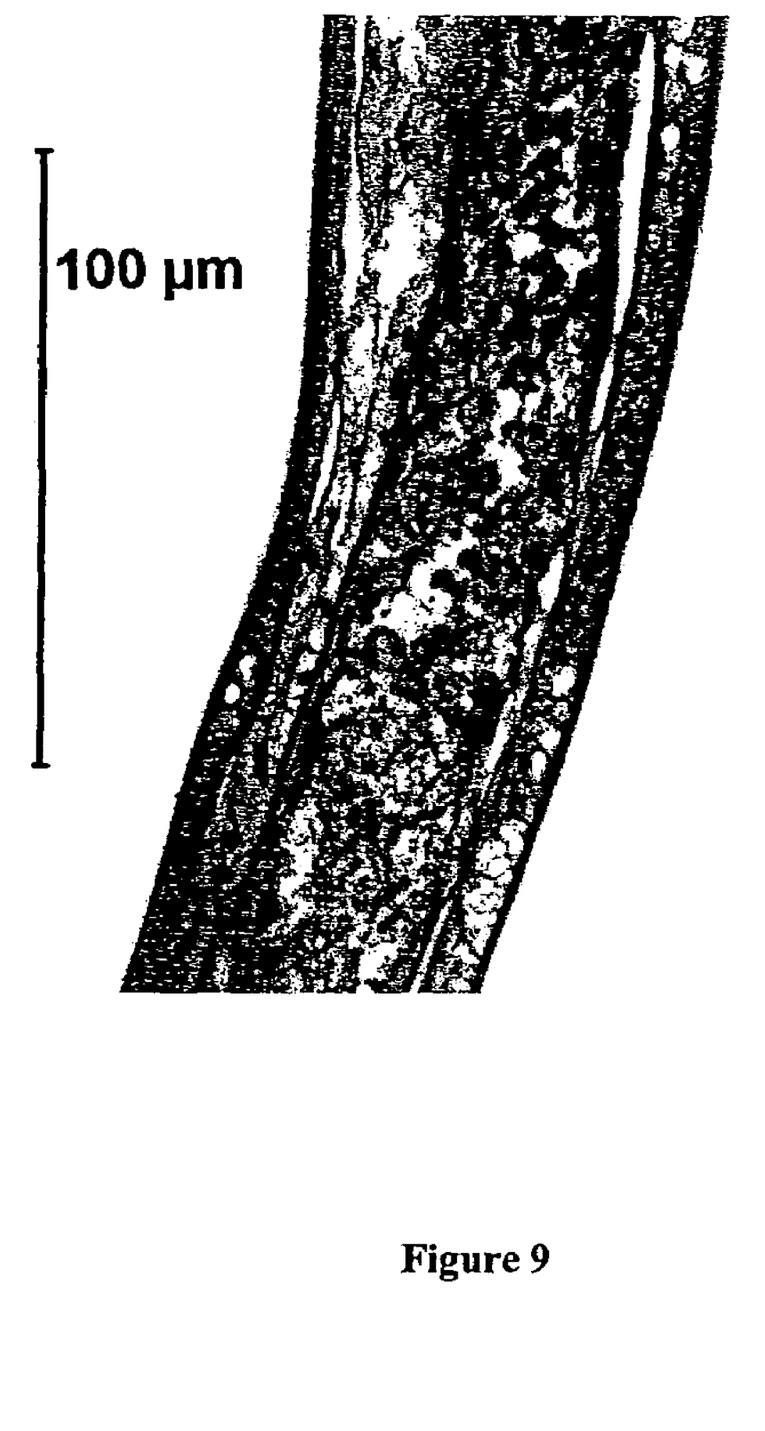
FIG. 9 is a longitudinal sectional view of adult male *B. malayi* killed by 5 ppm compound B. Note marked loss of cellularity in hypodermal and deeper structures. Magnification×400.

A single step synthesis of anthraquinone analogues (A-N) was accomplished by reacting selected phthalic anhydrides with substituted phenols in the presence of AlCl$_3$/NaCl (FIGS. 1 and 4). The reaction between phthalic anhydride and substituted phenols such as catechol, 1,4-hydroquinone and pyrogallol produced 1,2 dihydroxy-(A), 1,4-dihydroxy-(E) and 1,2,3-trihydroxy anthraquinones (F), respectively, whereas with resorcinol afforded 1,3-dihydroxy anthraquinone (D) and 3',6' dihydroxyfluoran (D1). However, the reaction with 3-methyl catechol yielded 1,2-dihyroxy-3-methyl anthraquinone (B) and 1-methyl-2,3-dihydroxy anthraquinone (C) as the major and minor products, respectively. It is interesting to compare the yield of products with various substrates. The reaction of phthalic anhydride and catechol gave 50% of A whereas with 3-methyl catechol gave products B and C with 60% and 15% yield, respectively. Moreover, the reaction with 1,4-hydroquinone and pyrogallol afforded 80% of E and 75% of F, whereas with resorcinol gave 50% of D and 20% of D1. The variation in yield was probably due to acylation at ortho and para positions to the hydroxyl groups. There is no para position free in 1,4-hydroquinone and hence the acylation was at ortho to the hydroxyl groups to afford a high yield of product E. In the reaction between pyrogallol and phthalic anhydride, the acylium ion either substituted at ortho to 1-hydroxyl or 3-hydroxyl group or para position to 2-hydroxyl group to yield a single product F. However, with 3-methyl catechol, the possible substitution of the acylium ions were either ortho or para to hydroxyl groups or ortho to the methyl group and lead to two products B and C with different yields. In the reaction between phthalic anhydride and resorcinol, the potential substitutions of the acylium ion are at positions 2, 4 and 6. The reaction did not take place at position 2 with high electron density due to steric hindrance but it was favored at positions 4 and 6 to yield D. However, with excess amount of resorcinol gave another side product D1. Interestingly, catechol gave only product A due to substitutions at positions 3 and 6. It is clear that even if the acylium ion reacts at positions 4 or 5 in catechol, A would have been the only product due to ring closures at 3 or 6 positions. Friedel-Crafts ortho bisacylation reactions were also studied in the presence of various solvents with AlCl$_3$ (FIG. 2). Although benzene, toluene and nitrobenzene are solvents of choice for acylation reaction (Huffman, J. W., et al., J. Org. Chem., 37 487-490 (1972)), it was found that nitrobenzene was the only effective solvent for Friedel-Crafts "ortho acylation" reaction in our studies. It is important to compare the reactivity and yield of products between AlCl$_3$/C$_6$H$_5$NO$_2$ and AlCl$_3$/NaCl melt. Even with a poor yield, AlCl$_3$/C$_6$H$_5$NO$_2$ system needed longer time (>4 h) and high temperatures such as >215 C for the reaction to complete. The reaction also was carried out with phthaloyl chloride 1a, instead of phthalic anhydride. Phthaloyl chloride 1a was prepared by treating phthalic acid with excess amount of thionyl chloride at 80 C for 2 h. The reaction was carried out under identical conditions with AlCl$_3$/C$_6$H$_5$NO$_2$. There was no improvement in the yield of the products. However, with the AlCl$_3$/NaCl melt at 165 C, the reaction proceeded faster and gave a much higher yield (FIG. 2). The poor yield at higher temperatures was probably due to potential decomposition of phenolic compounds.

Figure 3:
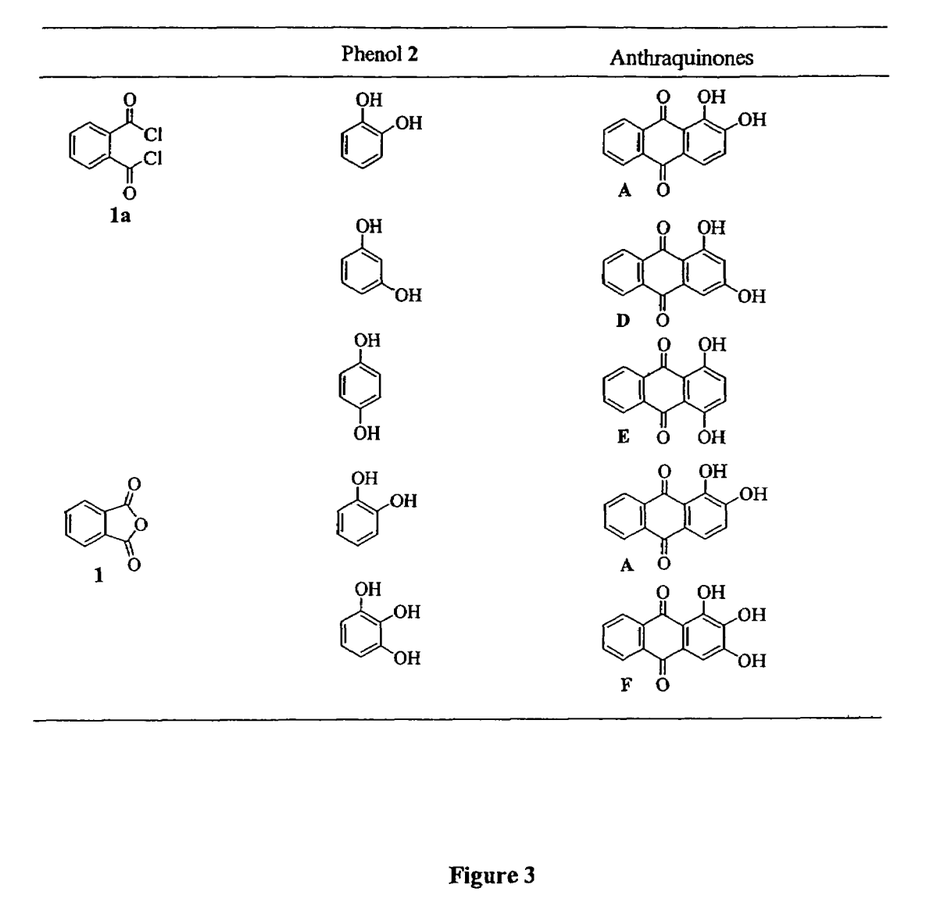
FIG. 3 is a schematic of the preparation of 3-hydroxyphthalic anhydride.

The anthraquinone J is one of the naturally occurring anthraquinones from daylily roots with significant activity against *Schistosoma mansoni* (Cichewicz, R. H., et al., Tetrahedron 58 8597-8606 (2002)). It was also found to be active against human filarial parasite, *B.malayi*. Therefore, J and its analogues were synthesized by Friedel-Crafts reaction by using 3-hydroxyphthalic anhydride and 3-methyl catechol as well as hydroxy phenols in general. Although 3-hydroxyphthalic anhydride is commercially available, it is very expensive to use as a synthon for their large-scale synthesis and evaluation as therapeutic drugs. The preparation of 3-hydroxyphthalic anhydride in poor yield was reported by Diels-Alder method by reacting maleic anhydride with 2-triethylsiloxyfuran followed by the aromatisation of the resulting cyclic adduct (Asaoka, M., et al., Chem. Lett. 167-170 (1977)). It was also prepared by using 3-aminophthalic anhydride (Eliel, E. L., et al., J. Am. Chem. Soc., 77 5092-5095 (1955)) or 3,6-diiodophthalic anhydride (Pratt, D. S., et al., J. Am. Chem. Soc. 40 219-214 (1918)) as synthons but resulted in very lower yield. A higher yield of 3-hydroxyphthalic anhydride was reported (Nasman, J-H. N., synthesis 788-789 (1985)) from 2-oxo-2,5-dihydrofuran, a commercially available and less expensive starting material for the production of 3-hydroxyphthalic anhydride. We have, therefore, synthesized 3-hydroxyphthalic anhydride by using the less expensive and commercially available 3-hydroxy butyrolactone as the starting material as shown in FIG. 3. The 3-Hydroxybutyrolactone (3) was treated with acetic anhydride in the presence of catalytic amount of concentrated sulfuric acid at 0° C. and then treated to 100° C. to yield 5-hydro-furan-2-one (4) over 90%. Compound 4 was then reacted with trimethylacetyl chloride in the presence of triethylamine at 0° C. to afford 2-furyl 2,2-dimethylpropionate (5). A mixture of 5 and maleic anhydride was then stirred at room temperature for overnight to form a Diels-Alder cyclic adduct, 6 (1-(2,2-Dimethylpropionyl)-4,10-dioxa-tricyclo [5.2.1.0$^{2,6}$]dec-8-ene-3,5-dione). The resulting product was then aromatized with concentrated sulfuric acid at −15° C. to afford 3-hydroxyphthalic anhydride (7).

The reaction between 3-hydroxyphthalic anhydride and catechol afforded three products 1,2,8-trihydroxy-, 1,2,5-trihydroxy- and 2,3,8-trihydroxy anthraquinones (I, H and G, respectively). However, 3-methyl catechol gave two products, 1,2,8-trihydroxy-3-methyl anthraquinone (J) and 1-methyl-2,3,8-trihydroxy anthraquinone (K). In addition, the reactions of 3-hydroxyphthalic anhydride with other phenols such as resorcinol, 1,4-hydroquinone, and pyrogallol produced 1,3,5-trihydroxy- (L) 1,4,8-trihydroxy- (M), and 1,2,3,5-tetrahydroxy anthraquinone (N), respectively. It is interesting to note that with the excess amount of resorcinol in the reaction mixture yielded one by-product, 4,3',6'-trihydroxyfluoran (L1).

The reaction of phthalic anhydride and catechol gave 30% of G and 10% of each H and I. Similarly, 3-methyl catechol and phthalic anhydride gave J and K in 30 and 15% yields, respectively. Also, the reactions of phthalic anhydride with resorcinol, 1,4-hydroquinone and pyrogallol afforded 35% of L, 55% of M and 50% of N, respectively. However, with an excess amount of resorcinol led to 40% of L and 20% of L1. The variation in yield demonstrated the acylium ion substitution at both the ortho and para positions to the hydroxyl groups. There was no para position free in 1,4-hydroquinone and hence the acylium ion substitution favored only at ortho to the hydroxyl groups and led to a single product M. In pyrogallol, acylium ion substituted either at ortho to 1-hydroxyl or 3-hydroxyl group to afford product N. However, in 3-methyl catechol, the possible substitution of acylium ions was either at ortho and para to hydroxyl groups or ortho to methyl group which led to two different products J and K. The reaction of phthalic anhydride with resorcinol indicated substitutions at positions 2, 4 and 6. Due to steric hindrance at position 2 (though it had a high electron density), the reaction did not favor at that position, but favored at positions 4 and 6 to yield L, which is ortho and/or para to both hydroxyl groups. However, an excess amount of resorcinol in the reaction mixture gave the side product, L1.

In order to study structure-activity relationship, methyl and methoxy derivatives of anthraquinones were prepared. The hydroxyl groups were protected by methylation. Selective mono-methylation of anthraquinones B and J at 2-hydroxyl group was carried out with diazomethane in ether at room temperature afforded 1-hydroxy-2-methoxy-3-methyl anthraquinone (O) and 1,8-dihydroxy-2-methoxy-3-methyl anthraquinone (Q). A similar methylation of anthraquinone K with $CH_2N_2$ yielded a dimethylated product, 1-methyl-2,3-dimethoxy-8-hydroxy anthraquinone (S). However, anthraquinones B, J and K with dimethylsulfate/$K_2CO_3$ in acetone at room temperature afforded 1,2-dimethoxy-3-methyl anthraquinone (P), 1,2-dimethbxy-8-hydroxy-3-methyl anthraquinone (R) and 1-methyl-2,3-dimethoxy-8-hydroxy anthraquinone (S), respectively. Compounds C, K, N, R and S are novel.

EXPERIMENTAL

Phthalic anhydride and 3-hydroxy phthalic anhydride (purchased or synthesized), catechol, 3-methlyl catechol, resorcinol, 1,4-hydroquinone, phyrogallol, anhydrous $AlCl_3$ and NaCl were purchased from Sigma-Aldrich. $^1H$ and $^{13}C$ NMR were recorded (DMSO-$d_6$ or $CDCl_3$) at 500 MHz on a Varian VRX instrument. DMSO-$d_6$ and $CDCl_3$ was purchased from Cambridge Isotope Laboratories, Inc., Andover, Mass. UV-VIS spectra were recorded in $CH_3OH$ using a Shimatzu (UV-260) spectrophotometer. C-18 silica gel (32-63 μm) was obtained from Fisher Scientific, Pa.

Preparation of 5-hydro-furan-2-one (4)

3-hydroxy butyrolactone (3) (10 mmol, 0.779 ml) and acetic anhydride (10 mmol, 0.95 ml) were mixed in an RB and 2 drops of conc. $H_2SO_4$ was added at 0° C. The pale yellow solution became dark yellow. The reaction mixture was stirred for 15 min. DMAP was added to neutralize $H_2SO_4$ and heated at 100° C. for 3 h in an oil bath. The reaction mixture was distilled at atm pressure to remove acetic acid and followed by vacuum distillation to yield the desired product, 4 (90% yield). $^1H$ NMR ($CDCl_3$): δ 4.83(m, 2H), 6.06 (m, 1H), 7.56 (m, 1H). $^{13}C$ NMR ($CDCl_3$): 72.11, 121.00, 153.22, 173.76.

Preparation of 2-furyl 2,2-dimethylpropionate (5)

A solution of triethylamine (6 mmol, 0.83 ml) in acetonitrile (5 ml) was added drop wise to a solution of 5-hydrofuran-2-one (5 mmol, 0.35 ml) and trimethylacetyl chloride (6 mmol, 0.74 ml) in acetonitrile (20 ml) and stirred at 60° C. for 4 h. The precipitate formed, triethylamine hydrochloride, was filtered off. The filtrate was washed with 10% sodium carbonate, dried over $MgSO_4$, distilled off the acetonitrile and the resulting product distilled under vacuum to yield product 5 (80%).

Preparation of 1-(2,2-Dimethyl-propionyl)-4,10-dioxa-tricyclo[5.2.1.0$^{2,6}$]dec-8-ene-3,5-dione (6)

2-furyl-2,2-dimethylpropionate (5 mmol, 840 mg) and maleic anhydride (5 mmol, 0.490 g) are dissolved in ether (1 ml/mmol of 5) and stirred overnight. The precipitate, product 6, was filtered off and crystallized from chloroform (75% yield): $^1H$ NMR (DMSO): δ 1.32 (s, 9H), 3.39 (d, 1H, J=7.0) 3.78 (d, 1H, J=7.0) 5.33 (d, 1H, J=2.0) 6.70 (m, 2H); $^{13}C$ NMR (DMSO): 176.68, 169.43, 166.10, 138.16, 137.33, 111.76, 52.87, 52.84, 48.92, 48.15, 48.09, 39.33, 27.10.

Preparation of 3-hydroxyphthalic anhydride (7)

Compound 6 (1 mmol, 266 mg) was added in small portions to 98% $H_2SO_4$ (2 ml) at 15° C. The cream colored mixture was stirred for 5 min and then poured over crushed ice. The precipitated product was filtered off, washed with ice-cold water and dried in a desiccator to afford product 7 (73%). $^1H$ NMR ($CD_3OD$): δ 7.40 (d, 1H, J=8.1) 7.62 (d, 1H, J=6.9), 7.85 (t, 1H, J=7.8).

General Method for the Preparation of Anthraquinones:

A mixture of anhydrous $AlCl_3$ (5 mmol, 0.667 g) and prebaked NaCl (2.5 mmol, 0.145 g) was heated (110° C.) in an oil bath till molten. A homogenous mixture of phthalic anhydrides, (1 mmol) and substituted phenols, (1 mmol) were reacted with $AlCl_3$/NaCl melt. The temperature was slowly increased and maintained at 165° C. for 4 h. The reaction mixture was cooled to 0° C., 10 ml of 10% HCl added, stirred for 15 min at 0° C. and refluxed at 100° C. for 30 min. The reaction mixture was cooled to room temperature and extracted with ethyl acetate. The resulting product was purified by $C_{18}$ MPLC column using acetonitrile:water (1:1) as the mobile phase.

General Method for the Preparation of Mono Methylated Anthraquinones:

Diazomethane was made by reacting N-nitroso-N-methylurea with KOH in ether. The anthraquinones (0.1 mmol) was dissolved separately in 2 ml of dry ether, cooled in an ice bath and the diazomethane in ether added in excess. The reaction mixture was allowed to stand for several hours, evaporated the solvent under reduced pressure and the resulting product purified by silica MPLC using 30% ethyl acetate in hexane as the mobile phase.

General Method for the Preparation of Dimethylated Anthraquinones:

The anthraquinone (0.1 mmol) was stirred with dry acetone (2 ml) and $K_2CO_3$ (0.1 mmol, 0.014 g). The reaction mixture was cooled in an ice bath. Dimethylsulphate (0.2 mmol) was added and allowed to stir for several hours at room temperature. The solvent was evaporated under vacuum, the residue dissolved in water and extracted with ethyl acetate. The resulting residue was purified by silica MPLC using 20% ethyl acetate in hexane as the mobile phase.

1,2-Dihydroxy anthraquinone (A)

UV $λ_{max}$ ($CH_3OH$) (log ϵ): 205 (4.47), 246 (4.6), 275 (4.4), 431 (3.7). $^1H$ NMR (DMSO): δ 7.27 (d, 1H, J=8.5), 7.70 (d, 1H, J=8.5), 7.95 (m, 2H), 8.23 (m, 2H). $^{13}C$ NMR (DMSO): 190.25, 182.03, 154.2, 152.28, 136.57, 135.51, 135.04, 134.16, 128.59, 127.95, 125.26, 122.70, 122.31, 117.73. Yield: 55%.

1,2-Dihydroxy-3-methyl anthraquinone (B)

UV $λ_{max}$ ($CH_3OH$) (log ϵ): 206 (4.46), 245 (4.36) 270 (4.39), 280 (4.39), 417 (3.57); $^1H$ NMR (DMSO): δ 2.32 (s, 3H), 7.61 (s, 1H), 7.94 (m, 2H), 8.21 (m, 2H). $^{13}C$ NMR (DMSO): 189.87, 182.17, 151.61, 151.11, 136.47, 135.48, 134.99, 134.29, 133.48, 128.18, 127.82, 124.57, 124.02, 115.96, 17.90. Yield: 60%.

1-Methyl-2,3-dihydroxy anthraquinone (C)

$^1H$ NMR (DMSO): δ 2.63 (s, 3H), 7.61 (s, 1H), 7.85 (m, 2H), 8.10 (dd, 1H, J=7.0, 1.5), 8.14 (dd 1H, J=7.5, 1.5); $^{13}C$

NMR (DMSO): 183.76, 182.07, 149.64, 149.39, 134.65, 133.89, 132.24, 128.00, 127.48, 126.55, 125.74, 124.90, 111.12, 110.96, 13.61. Yield: 60%.

1,3-Dihydroxy anthraquinone (D)

UV $\lambda_{max}$ (CH$_3$OH) (log ε): 211 (4.18), 282 (3.89), 311 (3.69), 410 (3.41); $^1$H NMR (DMSO): δ 5.73 (s, 1H), 6.59 (s, 1H), 7.72 (t, 1H, J=7.5), 7.83 (t, 1H, J=7.5), 8.07 (d, 1H, J=7.5), 8.13 (d, 1H, J=8.0). Yield: 75%.

1,4-Dihydroxy anthraquinone (E)

UV $\lambda_{max}$ (CH$_3$OH) (log ε): 206 (4.51), 223, (4.54) 248 (4.64), 278 (4.20), 479 (4.02); $^1$H NMR (DMSO): δ 7.47 (s, 2H), 8.01 (m, 2H), 8.30 (m, 2H); $^{13}$C NMR (DMSO): 187.40, 157.40, 135.77, 133.61, 133.04, 127.38, 113.40. Yield: 80%.

1,2,3-Trihydroxy anthraquinone (F)

UV $\lambda_{max}$ (CH$_3$OH) (log ε): 207 (4.59), 243 (4.39), 283 (4.49), 410 (3.71); $^1$H NMR (DMSO): δ 7.29 (s, 1H), 7.91 (m, 2H), 8.18 (m, 2H); $^{13}$C NMR (DMSO): 187.63, 181.67, 152.72, 152.48, 139.65, 135.22, 134.79, 133.94, 133.77, 127.30, 126.94, 125.37, 111.03, 109.52. Yield: 75%.

2,3,5-Trihydroxy anthraquinone (G)

$^1$H NMR (DMSO): δ 7.28 (dd, 1H, J=8.0, 1.0), 7.47 (s, 1H), 7.51 (s, 1H), 7.61 (dd, 1H, J=7.5, 1.0), 7.71 (t, 1H, J=8.0). $^{13}$C NMR (DMSO): 187.69, 181.05, 161.32, 152.45, 151.71, 136.63, 133.46, 127.14, 126.15, 123.66, 118.72, 115.78, 113.21, 112.66. Yield: 30%

1,2,5-Trihydroxy anthraquinone (H)

$^1$H NMR (DMSO): δ 7.28 (d, 1H, J=8.5), 7.41 (dd, 1H, J=8.5, 1.5), 7.54 (d, 1H, J=8.5), 7.79 (dd, 1H, J=7.5, 1.5), 7.83 (t, 1H, J=8). $^{13}$C NMR (DMSO): 188.04, 186.57, 161.70, 153.61, 151.14, 136.66, 133.14, 124.63, 123.16, 121.48, 120.74, 118.83, 116.20, 115.92. Yield: 10%

1,2,8-Trihydroxy anthraquinone (I)

$^1$H NMR (DMSO): δ 7.26 (d, 1H, J=8.5), 7.57 (dd, 1H, J=8.5, 1), 7.68 (d, 1H, J=8), 7.21 (dd, 1H, J=7.5, 1), 7.83 (t, 1H, J=8). $^{13}$C NMR (DMSO): 192.59, 180.07, 161.34, 152.93, 150.57, 137.49, 133.83, 122.78, 123.73, 121.42, 120.98, 119.04, 116.18, 116.09. Yield: 10%

1,2,8-Trihydroxy-3-methyl anthraquinone (J)

$^1$H NMR (DMSO): δ 2.24 (3H, s), 7.32 (d, 1H, J=8.5 Hz), 7.54 (1H, s), 7.67 (d, 1H, J=7.5 Hz), 7.74 (t, 1H, J=7.5). $^{13}$C NMR (DMSO): 114.35, 115.94, 119.05, 122.87, 123.11, 123.73, 132.32, 132.75, 137.40, 149.38, 150.27, 161.26, 180.19, 192.26. Yield: 30%.

1-Methyl-2,3,8-trihydroxy anthraquinone (K)

$^1$H NMR (DMSO): δ 2.65 (3H, s), 7.19 (d, 1H, J=8.5 Hz), 7.60 (1H, s), 7.63 (d, 1H, J=7.5 Hz), 7.73 (t, 1H, J=8). $^{13}$C NMR (DMSO): 111.38, 116.73, 117.88, 123.74, 124.12, 127.71, 128.67, 132.68, 135.87, 149.63, 150.15, 161.25, 181.41, 190.31. Yield: 15%.

1,3,5-Trihydroxy anthraquinone (L)

$^1$H NMR (DMSO): δ 6.58 (d, 1H, 2.5 Hz), 7.14 (d, 1H, 2.5 Hz), 7.33 (dd, 1H, J=8.5, JJ=1 Hz), 7.68 (dd, 1H, J=7.5 Hz, JJ=1 Hz), 8.07 (d, 1H, J=7.5), 7.78 (t, 1H, J=8.0). $^{13}$C NMR (DMSO): 108.07, 108.37, 109.23, 115.67, 118.68, 124.0, 133.2, 134.64, 137.33, 161.65, 164.87, 185.09, 187.34. Yield: 35%.

1,4,8-Trihydroxy anthraquinone (M)

$^1$H NMR (DMSO): δ 7.41 (dd, 1H, J=8.0, 1.5 Hz), 7.80 (dd, 1H, J=7.5, 1.0 Hz), 7.84 (t, 1H, J=8.0). Yield: 55%.

1,2,3,-5-Tetrahydroxy anthraquinone (N)

$^1$H NMR (DMSO): δ 6.58 (d, 1H, 2.5 Hz), 7.14 (d, 1H, 2.5 Hz), 7.33 (dd, 1H, J=8.5, JJ=1 Hz), 7.68 (dd, 1H, J=7.5 Hz, JJ=1 Hz), 8.07 (d, 1H, J=7.5), 7.78 (t, 1H, J=8.0). $^{13}$C NMR (DMSO): 108.07, 108.37, 109.23, 115.67, 118.68, 124.0, 133.2, 134.64, 137.33, 161.65, 164.87, 185.09, 187.34. Yield: 50%.

1-Hydroxy-2-methoxy-3-methyl anthraquinone (O)

$^1$HNMR (CDCl$_3$): δ 8.27 (m, 2H), 7.79 (m, 2H) 7.67 (s, 1H), 4.02 (s, 3H), 2.39 (s, 3H); $^{13}$C NMR (CDCl$_3$): 17.03, 60.64, 115.91, 122.55, 127.02, 127.61, 127.85, 133.58, 133.93, 134.17, 134.85, 140.22, 152.14, 155.84, 182.30, 188.99. Yield: 80%.

1,2-Dimethoxy-3-methyl anthraquinone (P)

$^1$HNMR (CDCl$_3$): δ 8.26 (m, 2H), 7.77 (m, 2H) 7.99 (s, 1H), 4.06 (s, 6H), 2.41 (s, 3H); $^{13}$C NMR (CDCl$_3$): 17.03, 61.00, 61.54, 125.85, 126.19, 126.89, 127.33, 129.98, 132.98, 133.67, 134.22, 135.21, 139.42, 153.74, 158.33, 182.74, 183.05. Yield: 75%.

1,8-Dihydroxy-2-methoxy-3-methyl anthraquinone (Q)

$^1$HNMR (CDCl$_3$): δ 7.82 (dd, 1H, J=7.5, 1.0), 7.68 (t, 1H, J=8.0) 7.30 (dd, 1H, J=8.0, 1.0), 4.04 (s, 3H), 2.39 (s, 3H). Yield: 75%.

1-Hydroxy-2,8-dimethoxy-3-methyl anthraquinone (R)

$^1$HNMR (CDCl$_3$): δ $^1$HNMR (CDCl$_3$): δ 7.77 (s, 1H,), 7.61 (dd, 1H, J=8.4, 0.9) 7.58 (t, 1H, J=7.8), 7.27 (dd, 1H, J=8.1, 1.2), 4.05 (s, 3H), 3.87 (s, 3H), 2.76 (s, 3H). Yield: 80%

1-Methyl-2,3-dimethoxy-8-hydroxy anthraquinone (S)

$^1$HNMR (CDCl$_3$): δ 7.77 (s, 1H,), 7.58 (dd, 1H, J=7.5, 1.0) 7.60 (t, 1H, J=8.0), 7.27 (dd, 1H, J=8.5, 1.0), 4.05 (s, 3H), 3.87 (s, 3H), 2.77 (s, 3H); $^{13}$C NMR (CDCl$_3$): 14.71, 56.43, 60.88, 108.90, 117.38, 118.98, 124.77, 125.91, 132.61, 133.02, 135.83, 137.23, 152.69, 157.32, 162.55, 182.82, 190.58. Yield: 75%.

Table 1 shows a comparison of $^{13}$C-NMR chemical shifts of C9 and C10 carbons, color and melting points of isomeric anthraquinones synthesized.

TABLE 1

| Anthraquinones | C9 | C10 | Color |
| --- | --- | --- | --- |
| B | 189.87 | 182.17 | Dark Orange |
| C | 183.76 | 182.07 | Yellow |
| G | 187.69 | 181.05 | Yellow |
| H | 188.04 | 186.57 | Dark Orange |

TABLE 1-continued

| Anthraquinones | C9 | C10 | Color |
|---|---|---|---|
| I | 192.59 | 180.07 | Dark Orange |
| J | 192.26 | 180.19 | Dark Orange |
| K | 191.05 | 182.14 | Yellow |

TABLE 2 shows melting points and HRMS data for compounds A to S of the present invention.

| Anthraquinones | Melting point ° C. | Observed Mass by HRFAB, [MH$^+$] | Theoretical mass [M] |
|---|---|---|---|
| A | 173-174 | 241.0502 | 240.0423 |
| B | 224-225 | 255.0655 | 254.0679 |
| C | $^a$297-299 | 255.0658 | 254.0679 |
| D | 207-208 | 241.0500 | 240.0423 |
| E | 195-196 | 241.0500 | 240.0423 |
| F | 282.284 | 257.0449 | 256.0372 |
| G | $^a$302-304 | 257.0449 | 256.0372 |
| H | 263-264 | 257.0449 | 256.0372 |
| I | 234-235 | 257.0449 | 256.0372 |
| J | 239-240 | 271.0606 | 270.0528 |
| K | $^a$304-305 | 271.0606 | 270.0528 |
| L | $^a$284-286 | 257.0451 | 256.0372 |
| M | $^a$254-256 | 257.0450 | 256.0372 |
| N | $^a$278-279 | 273.0398 | 272.0321 |
| O | 154-155 | 269.0813 | 268.0736 |
| P | 127-128 | 283.0970 | 282.0892 |
| Q | 173-174 | 285.0761 | 284.0685 |
| R | 283-284 | 299.0920 | 298.0841 |
| S | 197-198 | 299.0920 | 298.0841 |

$^a$decomposition point

Antifilarial Assays:

EXAMPLE 1

A collection of 100 adult female *Brugia malayi* were obtained through an NIH subcontract from Dr. John McCall, University of Georgia in order to test the efficacy of anthraquinones as antifilarial agents. Three worms per well were transferred to 6 well plates containing fresh RPMI 1640 culture medium supplemented with L-glutamine and penicillin/streptomycin. Anthraquinones were dissolved in 100% DMSO at a concentration of 4 mg/ml, and diluted with RPMI media to obtain a final concentration of 50 ppm. Duplicate control groups received 2% DMSO or no DMSO. The medium was removed and replaced with fresh RPMI with or without drug in DMSO every 48 h. The movement and viability of the adult worms were monitored every 24 h till 10 days. The *B. malayi* worms in control wells were fully motile till the end of 10$^{th}$ day and the worms treated with anthraquinones were dead.

EXAMPLE 2

The anthraquinones A, B, D, E, F, J, Q and R, selected randomly, were assayed against adult female filarial (*Brugia malayi*) worms for mortality and inhibition of motility. The assay was conducted at 5 ppm of anthraquinones and the results are presented in Table 3. The result showed that anthraquinones B and R were the most active against *B. malayi* with 100% mortality in 24 h. Compound J also showed significant activity and displayed 100% mortality in 2 days. Other anthraquinones tested gave 100% mortality between 3-10 days (Table 3)

TABLE 3

Antifilarial Activity of Anthraquinones against *B. malayi* adult worms at 5 ppm

| Anthraquinones | 100% Mortality of *B. malayi* (Days) |
|---|---|
| A | 11 |
| B | 5 |
| C | 7 |
| D | No activity |
| E | 10 |
| F | 5 |
| G | 5 |
| H | 9 |
| I | 14 |
| J | 5 |
| K | 3 |
| L | 7 |
| M | 9 |
| N | 5 |
| O | No activity |
| P | 11 |
| Q | No activity |
| R | 7 |
| S | 9 (50% activity) |
| RPMI | No activity |
| RPMI + 2.5% DMSO | No activity |
| Albendazole positive control | 16 |

The controls, treated with DMSO solvent, showed no mortality or inhibition of motility even after 20 days. Te assay was repeated with anthraquinones B, F, J and R since they killed the worms quickly compared to the other anthraquinones tested. A dose response study, ranging from 50 to 3.12 ppm, demonstrated 1005 mortality for compounds B at 3.125 ppm in 6 days, compound F at 3.125 ppm in 5 days, compound J at 6.25 ppm in 5 days and compound R at 6.25 ppm in 8 days (Table 4).

TABLE 4

Dose response of active anthraquinones, B, F, J and R against *B. Malayi* adult worms

| Concentration (ppm) | 100% Mortality of *B. Malayi* (Days) | | | |
|---|---|---|---|---|
| | B | F | J | R |
| 50 | 1 | 2 | 2 | 1 |
| 25 | 3 | 4 | 3 | 2 |
| 12.5 | 4 | 4 | 4 | 4 |
| 6.25 | 5 | 5 | 5 | 8 |
| 3.125 | 6 | 5 | No Mortality | No Mortality |
| RPMI | No Mortality | No Mortality | No Mortality | No Mortality |
| RPMI + 2% DMSO | No Mortality | No Mortality | No Mortality | No Mortality |

EXAMPLE 3

Live adult male and female *B. malayi* were obtained from John McCall, University of Georgia, Athens, Ga. (NIH Subcontract). Adult worms were transferred to 6 well plates (3 worms, male or female per well) containing fresh RPMI 1640 culture medium supplemented with L-glutamine and penicillin/streptomycin. Anthraquinones were dissolved separately in 100% DMSO (4mg/ml) and diluted with RPMI media to obtain a final concentration of 5 ppm. Duplicate control groups received 2.5% DMSO or no DMSO. Every 48 h, the medium from each well was removed and replaced with fresh RPMI with or without drug in DMSO. The movement and mortality of the filarial were monitored every 24 h for 20 days. All *B. malayi* worms in control wells were fully motile throughout the study and the worms treated with anthraquinones were dead. The results are summarized in